(12) United States Patent
Hiremath

(10) Patent No.: US 8,392,166 B2
(45) Date of Patent: Mar. 5, 2013

(54) METHOD FOR PROVIDING A NUMERICAL AND GRAPHICAL ABBREVIATED PROFILE OF A DRUG (A-POD)

(76) Inventor: Chaitanya N. Hiremath, Westford, MA (US)

(*) Notice: Subject to any disclaimer, the term of this patent is extended or adjusted under 35 U.S.C. 154(b) by 1114 days.

(21) Appl. No.: 12/209,319

(22) Filed: Sep. 12, 2008

(65) Prior Publication Data

US 2009/0125249 A1 May 14, 2009

Related U.S. Application Data

(60) Provisional application No. 60/994,811, filed on Sep. 22, 2007.

(51) Int. Cl.
*G06G 7/48* (2006.01)
(52) U.S. Cl. ........................................... 703/11
(58) Field of Classification Search ........................ None
See application file for complete search history.

(56) References Cited

PUBLICATIONS

Rust et al. (J. Chem. Inf. Comput. Sci. 2003, 43, 757-772).*
Generate MD (User Manual, Version 2.0.1, 2003, pp. 1-7, website: http://www.chemaxon.com/jchem/doc/user/GenerateMD.html).*
Muegge (Medicinal Research Reviews, 2003, vol. 23, No. 3, p. 302-321).*
Subramanian (Expert Opinion on Drug Metabolism & Toxicology, vol. 1, No. 3 , p. 555-564), Published in 2005.*
Kerns (Journal of Pharmaceutical Sciences, 2001, vol. 90, No. 11, p. 1838-58).*
Hiremath, CN. Abbreviated Profile of Drugs (A-POD): A unique numerical and graphical representation for compound properties and its use in ADMET prediction. International Journal of Integrative Biology (2007). 1(1): 44-50. Accepted on Aug. 30, 2007. Published online on Sep. 1, 2007. The International Journal of Integrative Biology (ISSN 0973-8363)—is an online journal for biology beyond borders. http://www.classicrus.com/IJIB/Arch/2007/1009.pdf.

* cited by examiner

*Primary Examiner* — Pablo S Whaley

(57) ABSTRACT

A novel numerical and graphical representation has been developed to better comprehend the physicochemical, biological and pharmacokinetic properties of drug-like compounds. Abbreviated profile of drug (A-POD) would help in considering and visualizing the various compound characteristics as one entity. The salient features of A-POD are: a unique way of representing the compound properties, computer friendly numerical string representation making comparison of any properties possible, graphical representation that gives a snapshot of properties and their relative changes, and its usefulness in qualitatively predicting the ADMET properties based on chemical properties alone. This simple yet powerful web-based tool is especially useful in comparing any two compounds at one time. A new therapeutic agent can be compared with the reference compound quickly and easily, by checking which properties are affected and finding out whether it possesses better drug-like properties.

3 Claims, 7 Drawing Sheets

METHOD FOR PROVIDING A NUMERICAL AND GRAPHICAL ABBREVIATED PROFILE OF A DRUG (A-POD)

CROSS-REFERENCE TO RELATED APPLICATIONS

This patent application is related to U.S. patent provisional application No. 60/994,811, "Abbreviated Profile of Drugs (A-POD): A unique numerical and graphical representation for compound properties and its use in ADMET prediction", filed on Sep. 22, 2007.

BACKGROUND ART

Blake J F (2000). Chemoinformatics—predicting the physicochemical properties of 'drug-like' molecules. *Curr Opi Biotech.* 11: 104-107.

Ertl P et al. (2000). Fast calculation of molecular polar surface area as a sum of fragment based contributions and its application to the prediction of drug transport properties. *Med Chem.* 43: 3714-3717.

Ertl P et al. (2003). Web-based cheminformatics and molecular property prediction tools supporting drug design and development at Novartis. *SAR and QSAR in Environmental Research.* 14: 321-328.

Helson H E (1999). Structure diagram generation. Edited by Lipkowitz KB & Boyd DB. *Rev Comput Chem.* 313-398.

Hodgson J (2001). ADMET—turning chemicals into drugs. *Nature Biotech.* 19: 722-726.

Kubinyi K J (2002). Chemical similarity and biological activities. *Baz Chem Soc.* 13(6): 717-726.

Lipinski C A et al. (1997). Experimental and computational approaches to estimate solubility and permeability in drug discovery and development settings. *Adv Drug Deliv Rev.* 23: 3-25.

Lombardo F et al. (2003). In silico ADME prediction: Data, models, facts and myths. *Mini Reviews in Medicinal Chemistry.* 3: 861-875.

Pajouhesh H & Lenz GR (2005). Medicinal chemical properties of successful central nervous system drugs. *NeuroRx.* 2: 541-553.

Stenberg P et al. (2001). Experimental and computational screening models for the prediction of intestinal drug absorption. *Med Chem.* 44: 1927-1937.

Subramanian K (2005). truPK—Human pharmacokinetic models for quantitative ADME prediction. *Expert Opin Drug Metab Toxicol.* 1(3): 555-564.

Van de Waterbeemd H et al. (2001). Property-based design: optimization of drug absorption and pharmacokinetics. *J Med Chem.* 44: 1313-1333.

Weininger D (1988). SMILES, a chemical language and information system. Introduction to methodology and encoding rules. *J Chem Inf Comput Sci.* 28: 31-36.

STATEMENT REGARDING FEDERALLY SPONSORED RESEARCH OR DEVELOPMENT

Not applicable.

REFERENCE TO A COMPUTER PROGRAM LISTING

There are three computer programs that are involved for A-POD:
1. File name: Hiremath_A-POD_Program_Compute.txt
   This first program is executed from the computer in an internet browser. It accepts the text file containing the compound related information and then processes it to generate the A-POD for the compound which also predicts the pharmacokinetic properties.
2. File name: Hiremath_A-POD_Program_PredictADMET.txt
   This second program is run by the processor. It accepts the A-POD of a single compound computed from the first program and displays the results on the computer in an internet browser.
3. File name: Hiremath_A-POD_Program_ProfileDifference.txt
   This third program is run by the processor. It accepts the A-POD for the two compounds computed from the first program and displays the results on the computer in an internet browser.

FIELD OF THE INVENTION

The present invention relates to the computational drug discovery methods and systems for a unique, numerical and graphical, A-POD representation of any number of physicochemical, biological, and pharmacokinetic properties of chemical compounds. Unlike other prediction methods of pharmacokinetic properties which are based on modeling and analysis of other compounds, the present invention is related to the prediction of pharmacokinetic properties based on the given compound's physicochemical properties alone, directly into the novel A-POD representation.

BACKGROUND OF THE INVENTION

In the early drug discovery process, one of the first steps is to find a reasonable and promising compound for a predefined target. This lead is then modified iteratively to optimize the biological activity. The compounds are synthesized and biologically evaluated for better activity. There are several physicochemical properties that need to the considered while designing or modifying compounds, so that these properties remain within the acceptable limits. Currently, these properties are computed and stored separately in a text file, spread sheet or database (Ertl et al., 2003). It is relatively easy for a chemist to comprehend several compounds along with their properties. However, this comprehension ability could be a challenge for a non-chemist. Hence, it is necessary to have a simple representation for the profile of the compounds, which need not be exact. Herein, a unique approach developed to aid in the actual design process of the compounds is described.

The Lipinski "rule of five", which is widely cited, is useful in revealing the drug-like characteristics of compounds (Lipinski, et al., 1997). These are a set of four rules that the properties of a compound should satisfy to be drug-like. First, the molecular weight (MW) should be less than 500 daltons. The number of hydrogen-bond acceptors (HA) should be less than 10. The number of hydrogen-bond donors (HD) should be less than 5. Finally, the value of the octanol-water partition coefficient (LP) should be less than 5. These four rules have been mostly valid for several of the known drugs.

The polar surface (PS) area has been implicated as an important property for the drug-like compounds (Ertl, 2000; Blake, 2000). It is defined as the surface area ($Å^2$) occupied by nitrogen and oxygen atoms and their attached polar hydrogens. It is critical in the compound-membrane interactions (Pajouhesh & Lenz, 2005). The optimal polar surface area is considered to be under 90-120$Å^2$.

In spite of the some observed exceptions to the Lipinski's rule, the property values of the vast majority (90%) of the orally active compounds are within their cut-off limits (Lipinski, et al., 1997). Hence, the Lipinski properties as well as the polar surface area have been considered here.

Pharmacokinetic properties such as absorption, distribution, metabolism, excretion and toxicity (ADMET) are important in order to determine the success of the compound for human therapeutic use. The ideal oral drug is one that is rapidly and completely absorbed from the alimentary canal, distributed specifically to its site of action in the body, metabolized in a way that does not instantly remove its activity, and eliminated in a suitable manner, without causing any harm (Hodgson, 2001). ADMET is a complex phenomenon. It is estimated that around half of all drugs in development fail to make it to the market because of poor pharmacokinetics (Hodgson, 2001).

The pharmacokinetic properties depend on the chemical properties of the molecule. Stenberg and coworkers have found polar surface area to be a primary determinant of fraction absorbed (Stenberg, et al., 2001). Passive absorption also depends on the solution properties of the compound such as lipophilicity (octanol-water partition coefficient). Van de Waterbeemd and coworkers have suggested low molecular weight of compounds for oral absorption (Van de Waterbeemd, 2001). The distribution of the compound in the human body depends on factors such as blood-brain barrier (BBB), permeability, volume of distribution and plasma protein binding. The octanol-water partition coefficient has been implicated in the BBB penetration and permeability prediction, and so is the polar surface area (Pajouhesh & Lenz, 2005). Metabolism reduces the circulating drug concentration and increases elimination. Metabolism also influences oral bioavailability and toxicology of drugs (Pajouhesh & Lenz, 2005). It has been described by Lombardo and co-workers that the excretion process that eliminates the compound from the human body depends on the molecular weight and octanol-water partition coefficient. Rapid renal clearance is associated with small and hydrophilic compounds. The metabolism of most drugs that takes place in the liver is associated with large and hydrophobic compounds (Lombardo, et al., 2003). Higher lipophilicity of compounds leads to increased metabolism and poor absorption, along with an increased probability of binding to undesired hydrophobic macromolecules, thereby increasing the potential for toxicity (Pajouhesh & Lenz, 2005). These insights (summarized in Table 1) need to be incorporated into the discovery process.

Over the years, several quantitative structure-activity/property relation (QSAR/QSPR) approaches have been developed using large number of descriptors to predict the ADMET properties, with some success (Subramanian, 2005; Lombardo, et al., 2003). These in-silico prediction methods are mainly based on artificial neural networks; some of which are inaccurate, while others are time-consuming and are not practical. Therefore, a simple and quick method to predict ADMET properties from chemical structures is strongly needed for an effective drug design.

BRIEF SUMMARY OF THE INVENTION

The present invention, the abbreviated profile of drug, A-POD, is a unique representation for compound properties, which is extremely beneficial in several ways in the early design process of the compound against a pre-identified target. The computer friendly numerical string representation makes the comparison of any properties possible, where as the graphical representation gives a snapshot of properties and their relative changes. The importance of A-POD has also been demonstrated in prediction of ADMET, based on few chemical properties alone, directly into the A-POD representation. The invention provides methods and systems for not only a valuable "add-on" to standard property calculations but also a quick and qualitative predictor of ADMET that might aid in the day-to-day drug design efforts. The first-step has been taken towards unifying the physicochemical, biological, and pharmacokinetic properties in the A-POD representation.

DETAILED DESCRIPTION OF THE INVENTION

Abbreviated profile of drugs (A-POD), pronounced as A-pod, has been developed to better comprehend several of the important properties in a simple way. The numerical A-POD (NA-POD), pronounced as N-A-pod, is the string of numbers representing several relevant properties of compounds. NA-POD is computer friendly representation of the compound properties, similar to SMILES (Simplified Molecular Input Line Entry System) which is a line notation for representing the structure of molecules and reactions (Weininger, 1988). The graphical A-POD (GA-POD), pronounced as G-A-pod, is a visual representation of the selected compound properties. These two representations will aid in comprehending and visualizing the compound properties as a single entity. A-POD's usefulness is demonstrated in qualitative prediction of the ADMET properties based on chemical properties.

Selection of Compounds

Figure 1:
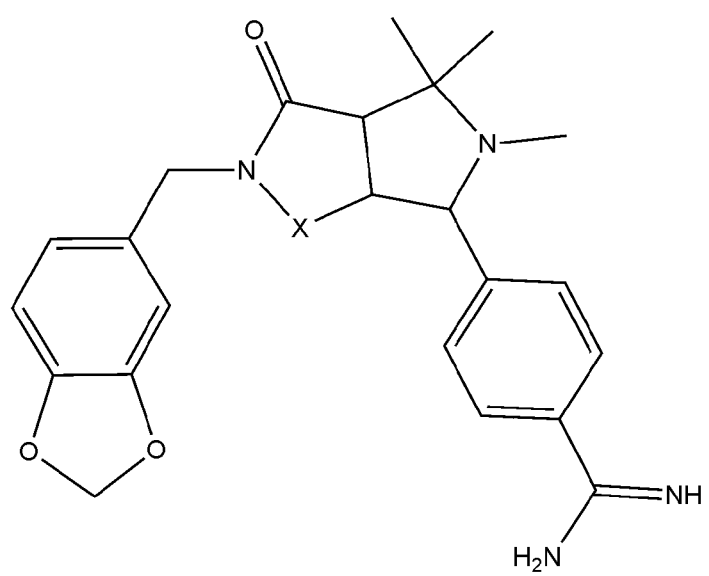
FIG. 1: Thrombin inhibitors: Analog which has X=—$CH_{2}$—with Ki=200 nM was considered as a reference compound and the analog which has X=—CO— with Ki=500 nM was considered as a "new" compound.

The compounds used for demonstration and analysis were selected based on the availability of low and high biological activity for a pair of similar compounds. For Thrombin inhibitors, analog containing X=—$CH_{2}$— with Ki=200 nM was considered as a reference compound and the analog containing X=—CO—with Ki=500 nM was considered as a "new" compound (FIG. 1). These compounds were selected from Kubinyi (Kubinyi, 2002).

Internet Tool

A web-based tool was created in the form of two Java applets. One applet was developed to display the physicochemical, biological, and pharmacokinetic properties for a given compound. And the other applet was developed to compare a "new" compound with a reference compound. Since, five dominant chemical properties (DCP) were used, the dependency relationships is referred to by the term "DCP5".

Convention

The order of the chemical properties considered is WRGLS, pronounced as wregals, where each letter corresponds to molecular weight (W), H-bond receiver (R), H-bond giver (G), lipophilicity (L), and polar surface area (S). For brevity, two letter codes are also used such as MW, HA, HD, LP, PS, respectively. These are followed by biological activity (BA) and absorption, distribution, metabolism, excretion, toxicity (ADMET). The complete order is therefore given by "WRGLSBADMET".

Polar Surface Area

Average polar surface area contributed by the oxygen, nitrogen, sulfur and phosphorous atom groups were computed based on the fragment contributions as described by Ertl and coworkers (Ertl, et al., 2000) (Table 2). Usually, oxygen and nitrogen atoms are considered in computing the polar surface area. Sulfur and phosphorous atoms could be considered in contributing partially to the polar surface area. The average conventional PSA(O, N) contribution is 16.45 $Å^2$ and the average comprehensive PSA(O, N, S, P) is 19.81 $Å^2$ (Table 2). Hence, comprehensive polar surface area is about 20% higher than the conventional polar surface area. The percentage of fraction absorbed with respect to the conventional polar surface area reaches a plateau around 125 $Å^2$. Coincidentally or naturally, in the spirit of the number five, the comprehensive polar surface area limit for the drug-like compounds could be considered as 150 $Å^2$. The Lipinski "rule of five" must then be expanded to include the comprehensive polar surface area, thereby making it the fifth rule (Table 3).

Normalization

Figure 2:
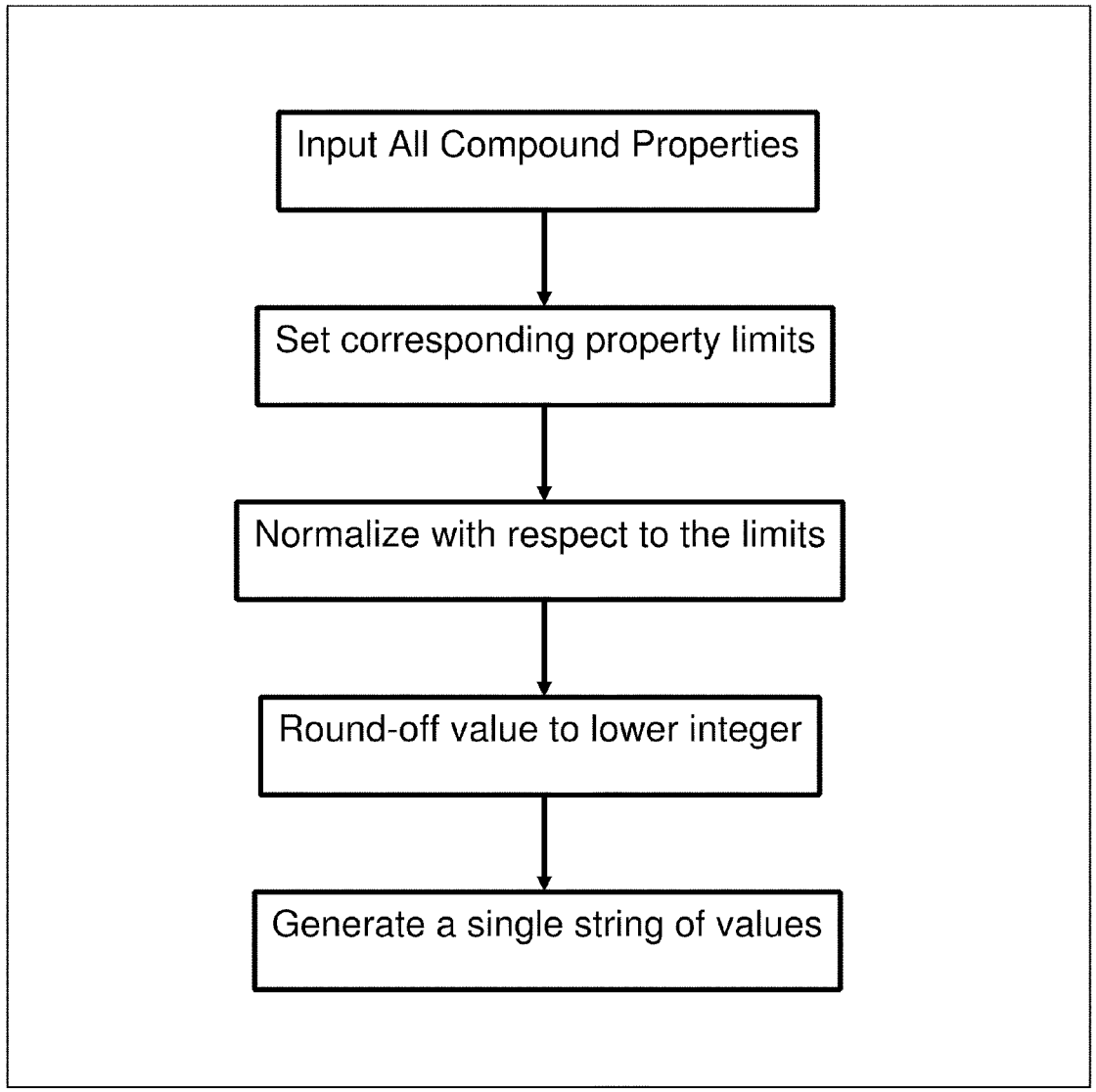
FIG. 2: The flowchart of a method of generating numerical presentation of compound properties.

In order to represent the properties of compound in a meaningful way, it is necessary to normalize them (FIG. 2). The normalization factor for a particular property is its upper limit for drug-like characteristic (Table 3). For numerical representation of the A-POD, it is first necessary to transform the properties of compounds into a simple common scale. The simplest scale could be numbers from zero through nine. Taking into account the upper limit for a given property, this property could be expressed in A-POD format by dividing the actual value of the compound property by its upper limit and then multiplying by the number ten. In order to obtain a single number, the normalized value must then be rounded off ("abbreviated") to the lowest integer. The property values that are violated are set to the upper limit 9 in the A-POD representation.

Biological Activity

The biological activity considered to be in the micro-molar to nano-molar range was normalized. The lower values correspond to higher efficacy of compounds. In contrast, the increase in the A-POD value represents the increase in biological activity of the compound. The inverse relationship was converted into a direct relationship by considering the one-minus-activity values. In order to easily identify the activity ranges, two groups with 5 values each were implemented; the micro-molar concentrations corresponding to A-POD values from 0 to 4, and the nano-molar concentrations corresponding to A-POD values from 5 to 9.

ADMET Prediction

Figure 3:
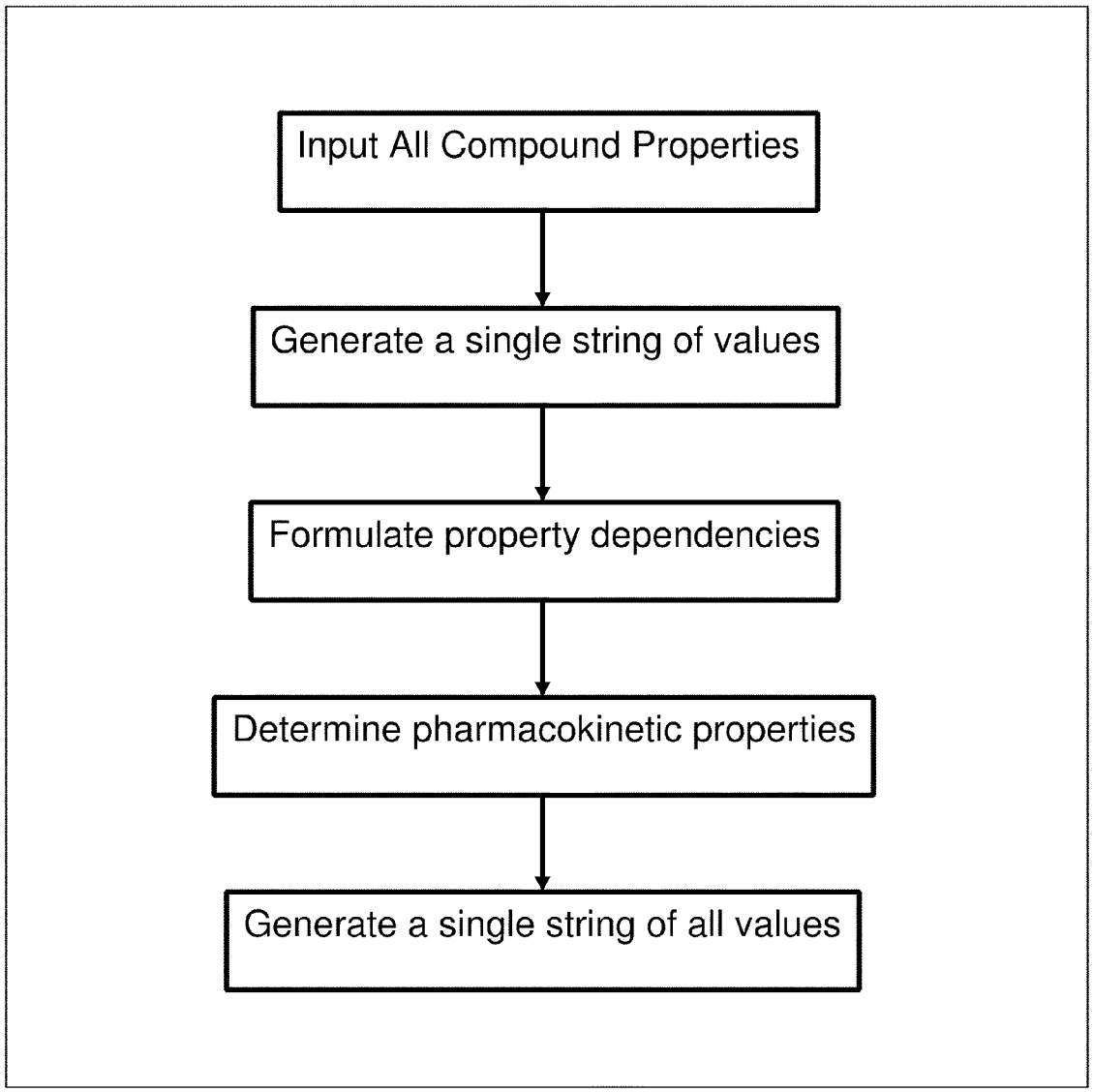
FIG. 3: The flowchart of a method of determination of pharmacokinetic properties.

The individual A or D or M or E or T property value was computed by considering the favorable and unfavorable relationships of the chemical properties as described earlier (Table 1). These relationships can be modified and updated as well. For example, if the molecular weight has opposite effect on absorption, then 1-minus-normalized molecular weight was considered for absorption. And if a particular pharmacokinetic property has more than two chemical property dependencies, then taking into account their direct or inverse dependency, a simple average was computed (FIG. 3).

Numerical A-POD

Considering several relevant properties as a string of numbers can represent the abbreviated profile of drug. For a hypothetical compound X after normalizing the compound property values, if molecular weight is 9, the number of hydrogen bond acceptors is 7, the number of hydrogen bond donors is 2, octanol-water partition coefficient is 4, and polar surface area is 6, the numerical A-POD may be written as A-POD(X: 97246). From this A-POD, it is clear that in considering the design of new compounds based on this compound, there is less room for increasing the molecular weight and more room in terms of increasing the properties such as the hydrogen-bond donors, partition coefficient and polar surface area. It is obvious that the actual molecular property values are not important in considering the modifications for a particular lead compound. The biological activity value can also be treated in the similar way. If the normalized biological activity for the hypothetical compound is 8, then the abbreviated profile for drug is A-POD(X:972468). Clearly, this hypothetical compound has the near-high biological activity and the compound is drug-like.

Graphical A-POD

Figure 4:
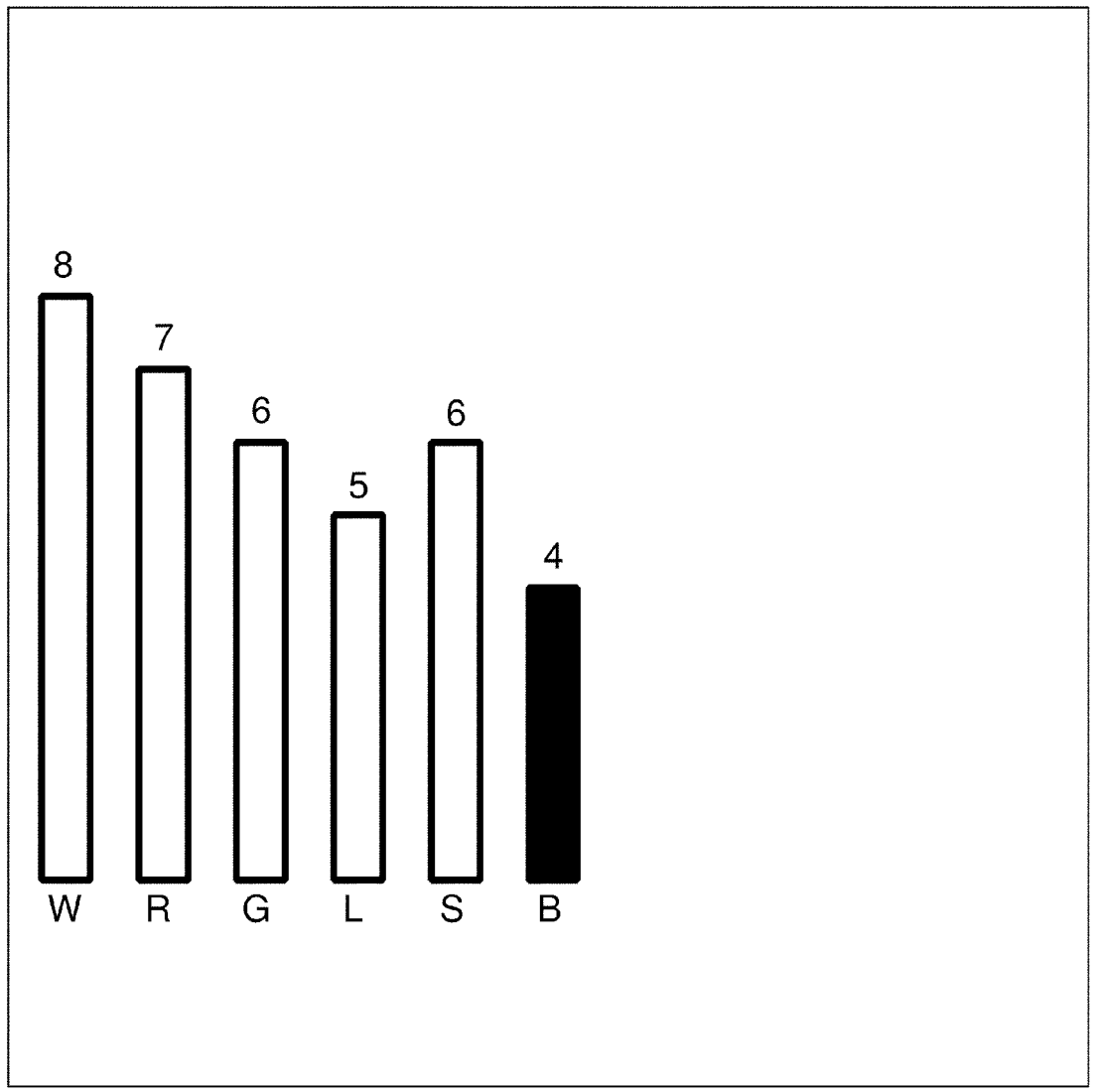
FIG. 4: Graphical representation of A-POD for the reference compound, with physicochemical and biological properties.

The graphical representation allows the non-chemist to have the chemist's memory of the compound. The physicochemical properties combined with the biological activity information for a compound capture useful drug information and make it easy to comprehend the profile of compound. Using these representations, even for a novice, it is extremely helpful to think of possible modifications to the compound and still be within the drug-like space. For thrombin inhibitor (FIG. 1), the graphical representation for the reference compound is shown (FIG. 4).

Comprehensive A-POD

Figure 5:
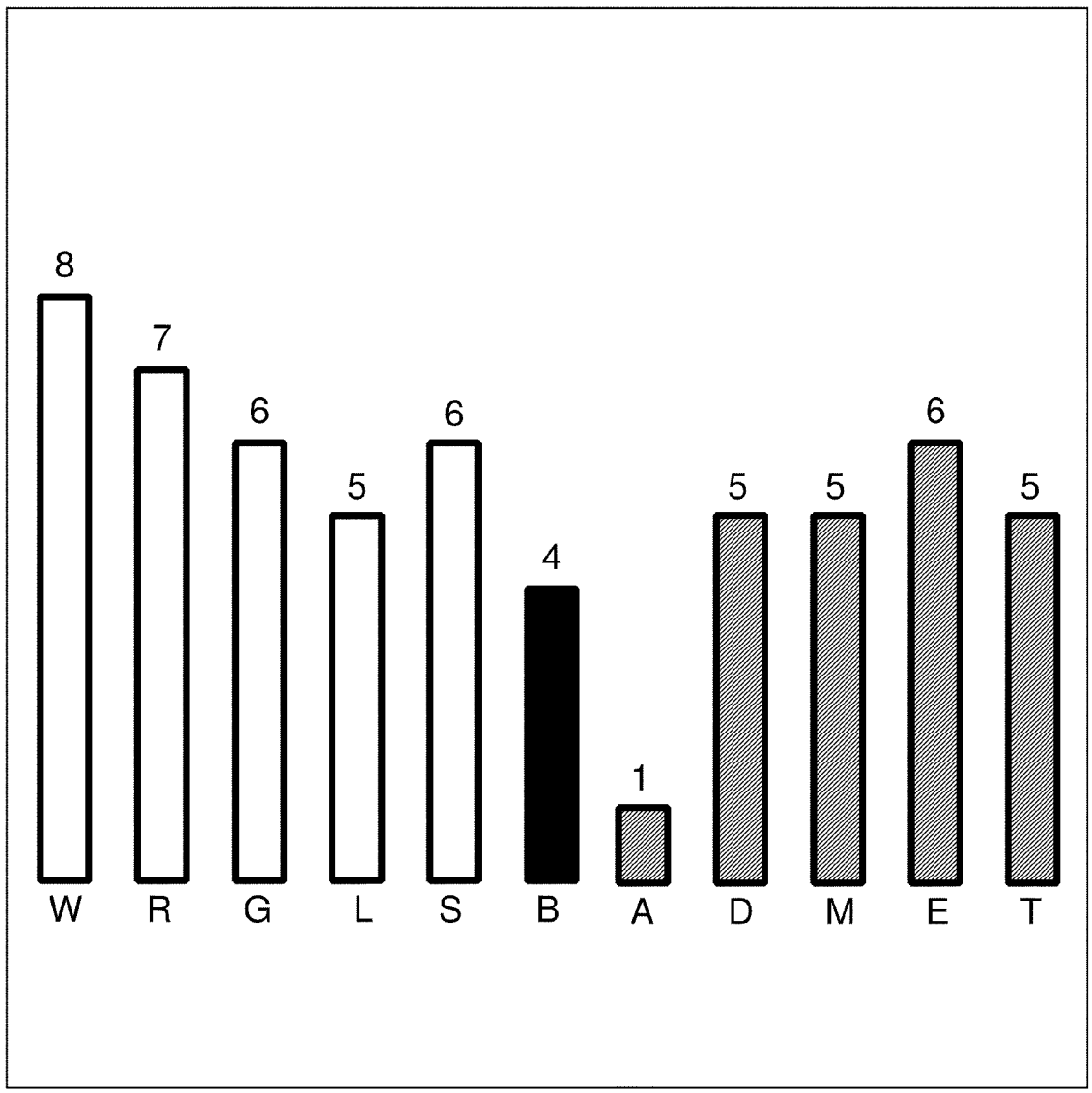
FIG. 5: Graphical representation of A-POD for the reference compound, with physicochemical, biological, and predicted pharmacokinetic properties.
Figure 6:
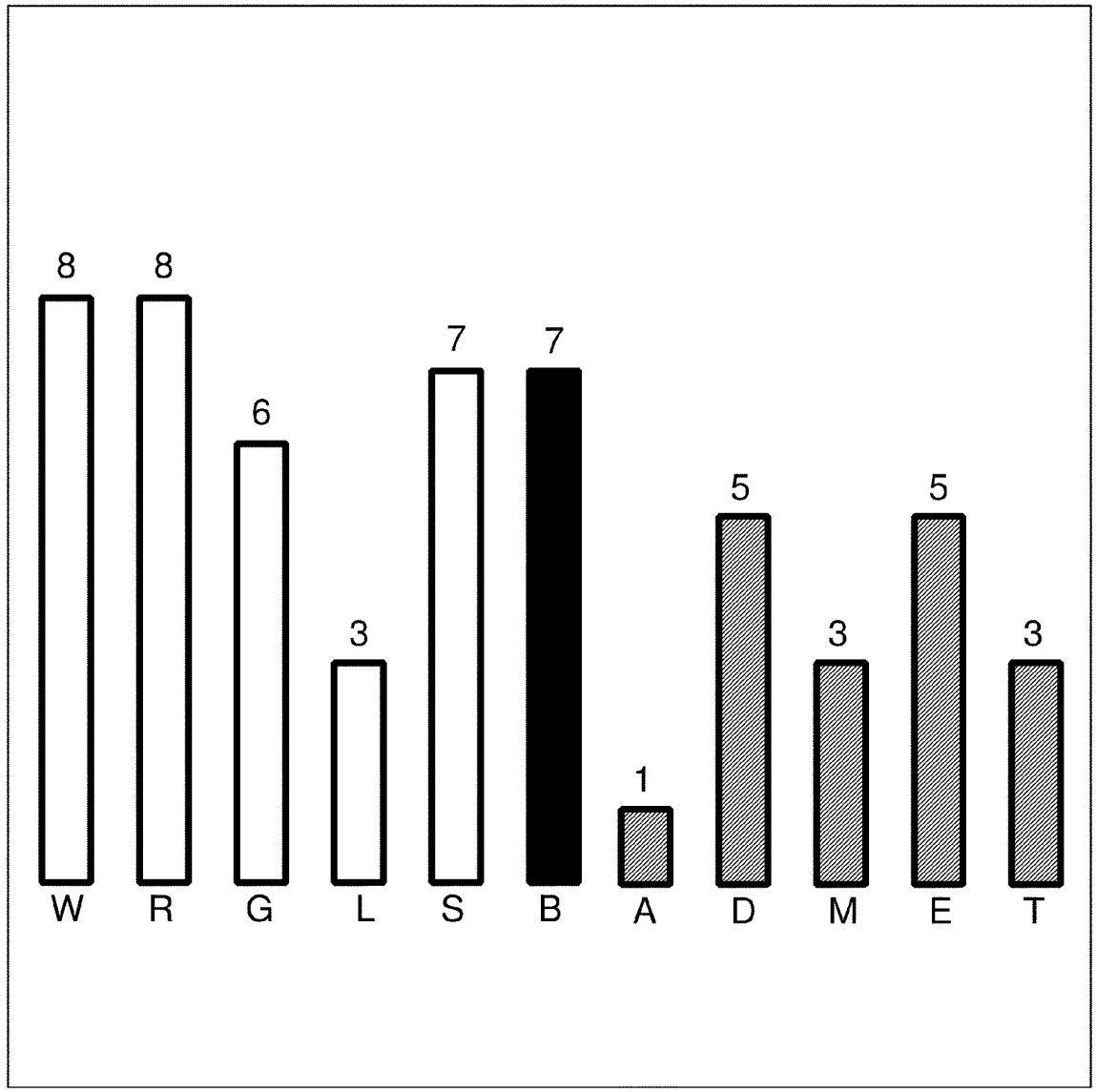
FIG. 6: Graphical representation of A-POD for the "new" compound, with physicochemical, biological, and predicted pharmacokinetic properties.

Here, an attempt has also been made to qualitatively predict the individual ADMET properties, based on a simple idea that a few chemical properties predominantly contribute to A, D, M, E or T (Table 1) (Stenberg, et al., 2001; Van de Waterbeemd, 2001; Pajouhesh & Lenz, 2005; Lombardo, et al., 2003). Applying the individual influences of the chemical properties to obtain pharmacokinetic properties, for both the numerical as well as graphical A-POD representations, gives a comprehensive A-POD, CA-pod, pronounced as C-A-pod. This unique way of determining individual pharmacokinetic properties could be customized and experimented by the user. For Thrombin inhibitor, the "new" compound clearly shows that not only the experimentally determined biological activity has improved but also predicts the unchanged absorption and distribution; improved/favorable properties such as metabolism, excretion and toxicity (reduced with respect to the reference compound) (FIG. 5 and FIG. 6). It is worth mentioning that, for the first time, the pharmacokinetics insights have been integrated and incorporated into the drug discovery process.

Difference A-POD

Figure 7:
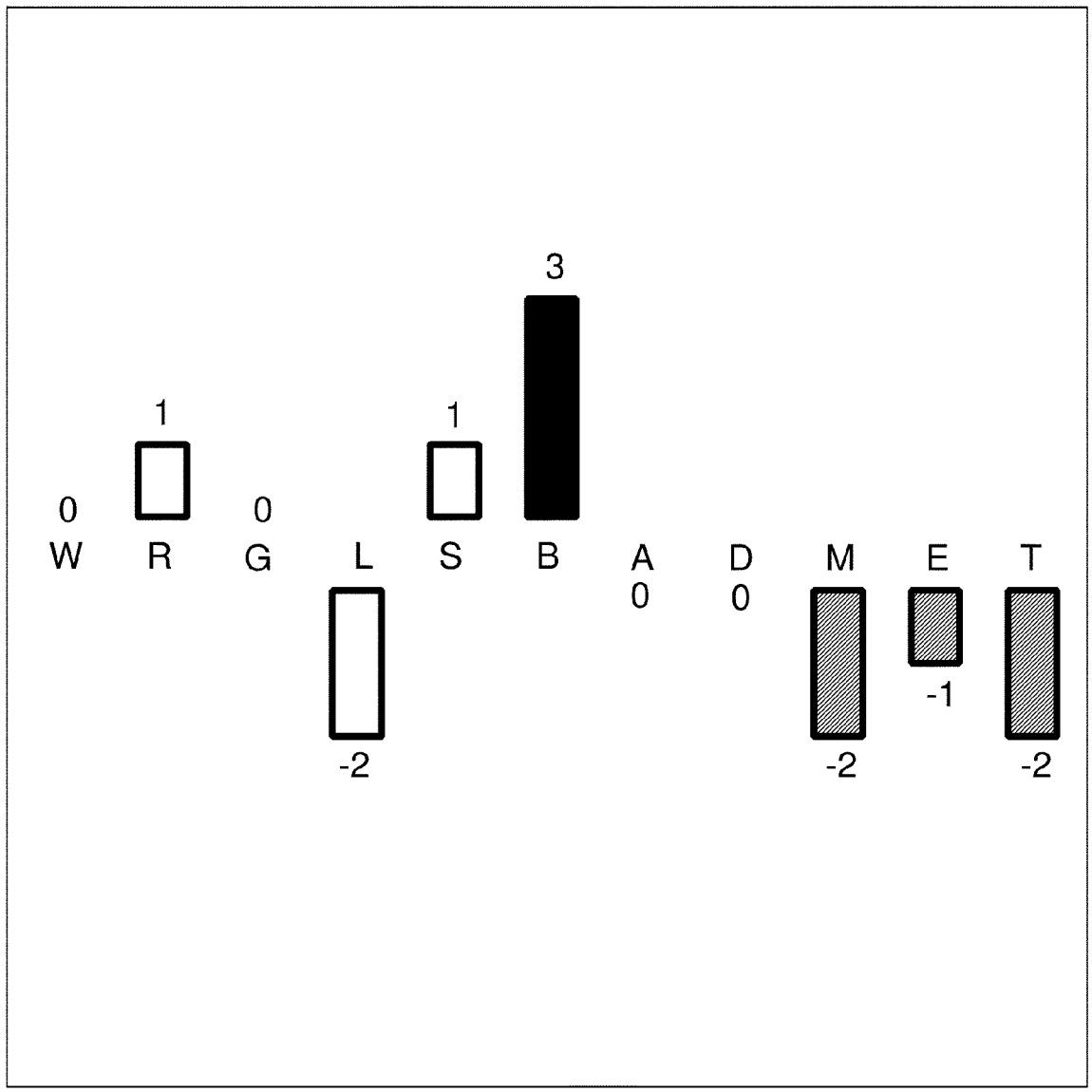
FIG. 7: Difference A-POD representation for the "new" compound with respect to a reference compound.

Difference A-POD, DA-pod, pronounced as D-A-pod, is useful in comparing two compounds. Since, the individual A-POD parameters are normalized, two corresponding parameters can be easily subtracted. The sum of all the difference A-POD values gives an overall effect of the modification made with respect to a particular reference compound. If the biological activity has improved for the new compound then the magnitude and direction for each property that changed can be taken as indication of the drug design going in the right direction. For Thrombin inhibitor, the DA-pod representation clearly shows which chemical properties are affected and its consequences on the ADMET properties (FIG. 7). The improvement in the biological activity is probably due to the increase in the number of hydrogen bond acceptors, decrease in the partition coefficient and increase in polar surface area. The improvement in the pharmacokinetic properties is also depicted.

Limitation of A-POD

The limitation of A-POD representation is that compounds must possess the properties within their range for drug-like compounds. It is primarily designed to help make a "good" lead compound into a "better" lead compound with "small" chemical changes, rather than starting with a "bad" compound.

Comparison of A-POD

The SMILES and A-POD representations are both linear notations related to the molecules, the former is a linguistic construct of structure where as the later is a mathematical construct of properties. SMILES strings can be converted back into the structures of the molecules. However, the conversion is not unambiguous (Helson, 1999). A-POD representation by design is not exact, and hence the individual values cannot be used for property conversion. Nevertheless, both SMILES and A-POD are simple, compact and computer friendly.

Unification of Properties in A-POD

The structure and the complex interplay between the various chemical properties of a compound are responsible for the biological efficacy of the compound and its pharmacokinetic properties such as ADMET. The changes in the chemical structure are made so as to maximize the efficacy of the compound with favorable ADMET properties. Thus, the profile of the compound should be considered as a single entity. It is incorrect to consider the ADMET properties separate from the chemical properties. Some of the chemical and biological properties may or may not be sufficiently independent of the others. It would not be worthwhile if the spatial and chemical properties do not produce optimal biological properties. Hence, it is likely that the complex interplay of the spatial and chemical properties as a whole is responsible for the biological properties. The precise value of the various properties may not be important. An attempt to take the first-step has been made towards unifying the chemical and biological properties in the A-POD representation.

TABLE 2

Average polar surface area contributed by the oxygen, nitrogen, sulfur and phosphorous atom groups.

| Polar atom present in the fragment | Contribution | Average PSA in Å$^2$ |
|---|---|---|
| O | Full | 16.69 |
| N | Full | 16.20 |
| S | Partial | 29.23 |
| P | Partial | 23.87 |

TABLE 3

Expanded Lipinski "rule of five"

| Rule | Property | Upper limit |
|---|---|---|
| 1 | Molecular Weight, Daltons (MW) | 500 |
| 2 | H-bond Acceptors (HA) | 10 |
| 3 | H-bond Donors (HD) | 5 |
| 4 | Octanol-Water partition coefficient (LP) | 5 |
| 5 | Comprehensive Polar Surface Area, Å$^2$ (PS) | 150 |

What I claim as my invention is:

1. A computer-implemented method for providing an abbreviated profile of a drug compound in a numerical representation to aid in drug design, said method comprising steps of:
   (i) defining a set of chemical, biological, and pharmacokinetic property parameters, wherein the set comprises molecular weight (W), hydrogen-bond acceptors (R), hydrogen-bond donors (G), octanol-water partition coefficient (L), and comprehensive polar surface area (S);
   (ii) obtaining, for one or more drug compounds, values associated with each of the property parameters and setting an upper and lower limit for each of said values;
   (iii) determining, for one or more drug compounds, a set of normalized values for each property parameter by dividing the values associated with each of the property parameters by its upper limit and multiplying the resulting number by ten;

TABLE 1

Chemical properties mainly contributing for pharmacokinetic properties

| ADMET Property | Pharmacokinetic property dependence on chemical properties | Favorable chemical property | Unfavorable chemical property | Other influencing ADMET properties |
|---|---|---|---|---|
| Absorption | Octanol-water partition coefficient; Polar surface area; Molecular weight; | A (lp, ps) | a (mw) | |
| Distribution | Octanol-water partition coefficient; Polar surface area; | D (lp, ps) | d ( ) | Absorption |
| Metabolism | Octanol-water partition coefficient; | M (lp) | m ( ) | Excretion; Toxicity |
| Excretion | Octanol-water partition coefficient; Molecular weight; | E (lp, mw) | e ( ) | Metabolism |
| Toxicity | Octanol-water partition coefficient; | T (lp) | t ( ) | Absorption |

(iv) determining, for one or more drug compounds, a set of abbreviated profile of drug compound (A-POD) values associated with each of the property parameters by rounding off the normalized values to the lowest integer, wherein the integers are between 0 and 9;

(v) generating, for one or more drug compounds, a numerical representation of the A-POD values associated with each of the property parameters defined as A-POD(X: WRGLS), wherein X represents the name of the drug, wherein W corresponds to the A-POD value associated with molecular weight; R corresponds to the A-POD value associated with hydrogen-bond acceptors; G corresponds to the A-POD value associated with hydrogen-bond donors; L corresponds to the A-POD value associated with octanol-water partition coefficient; and S corresponds to the A-POD value associated with comprehensive polar surface area; and (vi) displaying, for one or more drug compounds, the numerical representation of said A-POD values on a two-dimensional graph, wherein the A-POD values are displayed on the y-axis and the property parameters are displayed on the x-axis;

wherein steps (i)-(vi) are performed on a suitably programmed computer.

2. The method of claim 1 further comprising: repeating steps (i) through (v) using two different drug compounds, determining differences between the A-POD values associated with each of the property parameters for the two different drug compounds, and displaying the differences on a two-dimensional graph, wherein the differences between the A-POD values are displayed on the y-axis and the property parameters are displayed on the x-axis.

3. The method of claim 1 further comprising: generating and displaying an extended numerical representation of A-POD values associated with each of the property parameters by repeating steps (i) through (vi) using additional property parameters for biological activity (B); absorption (A); distribution (D); metabolism (M); excretion (E); and toxicity (T), wherein the extended numerical representation of A-POD values is defined as A-POD (X:WRGLSBADMET), wherein X represents the name of the drug, and wherein B corresponds to the A-POD value associated with biological activity; A corresponds to the A-POD value associated with absorption; D corresponds to the A-POD value associated with distribution; M corresponds to the A-POD value associated with metabolism; E corresponds to the A-POD value associated with excretion; and T corresponds to the A-POD value associated with toxicity.

* * * * *